United States Patent
Reverchon

(10) Patent No.: US 7,276,190 B2
(45) Date of Patent: Oct. 2, 2007

(54) PROCESS FOR THE PRODUCTION OF MICRO AND/OR NANO PARTICLES

(75) Inventor: Ernesto Reverchon, Salerno (IT)

(73) Assignee: Micro & Nano Materials SAGL, Lugano (CH)

( * ) Notice: Subject to any disclaimer, the term of this patent is extended or adjusted under 35 U.S.C. 154(b) by 574 days.

(21) Appl. No.: 10/482,640

(22) PCT Filed: Sep. 27, 2001

(86) PCT No.: PCT/IB01/01780

§ 371 (c)(1),
(2), (4) Date: Dec. 30, 2003

(87) PCT Pub. No.: WO03/004142

PCT Pub. Date: Jan. 16, 2003

(65) Prior Publication Data

US 2004/0178529 A1    Sep. 16, 2004

(30) Foreign Application Priority Data

Jul. 2, 2001   (CH) .................................. 1209/01

(51) Int. Cl.
*B29B 9/00* (2006.01)
(52) U.S. Cl. ............................. 264/5; 424/489; 425/6
(58) Field of Classification Search .............. None
See application file for complete search history.

(56) References Cited

U.S. PATENT DOCUMENTS 4,348,422 A    9/1982  Zosel
5,851,453 A *  12/1998 Hanna et al. ................... 264/5
5,874,029 A *   2/1999 Subramaniam et al. ....... 264/12

(Continued)

FOREIGN PATENT DOCUMENTS

DE        39 37 287 A        5/1991

(Continued)

OTHER PUBLICATIONS

Ventosa, Nora, et al., "Depressurization of an Expanded Liquid Organic Solution (DELOS): A New Procedure for Obtaining Submicron- or Micron-Sized Crystalline Particles", Crystal Growth & Design 2001 vol. 1, No. 4, 299-303, 2001 American Chemical Society, published on Web Jun. 14, 2001.

(Continued)

*Primary Examiner*—Mary Lynn Theisen
(74) *Attorney, Agent, or Firm*—Weingarten, Schurgin, Gagnebin & Lebovici LLP

(57) ABSTRACT

A process and an apparatus are proposed to perform the supercritical assisted atomization of nano and/or micro metric powders. It is possible to use liquid solvent at process conditions in which they show a low solubility in carbon dioxide. Atomization is obtained by solubilizing pressurized carbon dioxide (compressed, liquid, supercritical) in a solution formed by the solid to be micronized and the liquid solvent, solubilizing carbon dioxide up to near equilibrium conditions and then atomizing the solution down to near atmospheric conditions through a thin wall injector, to produce very small droplet of micronic and sub-micronic dimensions. The subsequent evaporation of the droplets produces particles with diameters ranging between 0.02 and 10 micron.

17 Claims, 3 Drawing Sheets

U.S. PATENT DOCUMENTS

Figure 1:
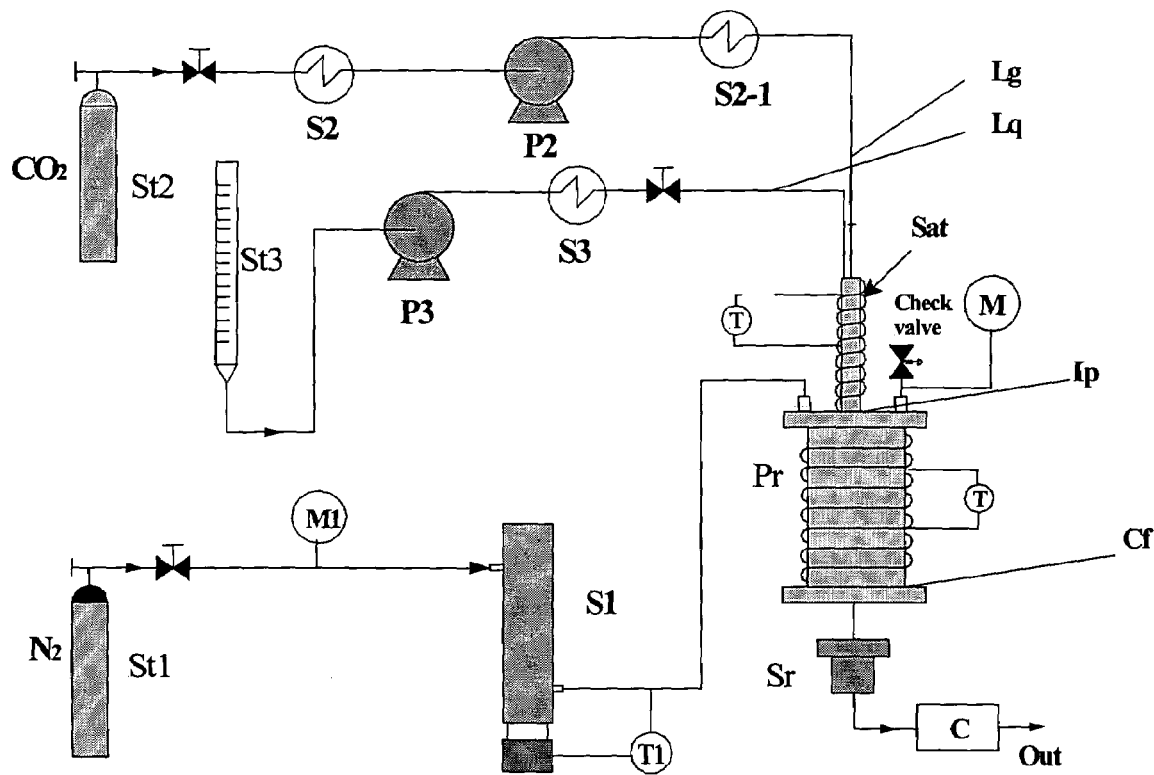

| | | | |
|---|---|---|---|
| 6,056,791 A | 5/2000 | Weidner et al. | |
| 6,221,153 B1 | 4/2001 | Castor et al. | |
| 6,475,524 B1 * | 11/2002 | Bisrat et al. | 424/489 |
| 2002/0018815 A1 * | 2/2002 | Sievers et al. | 424/489 |

FOREIGN PATENT DOCUMENTS

| | | |
|---|---|---|
| EP | 1 314 465 A1 | 5/2003 |
| WO | WO97 31691 A | 9/1997 |
| WO | WO 00 37169 A | 6/2000 |

OTHER PUBLICATIONS

Ullmann's Encyclopedia of Industrial Chemistry, 5$^{th}$ ed., vol. B3, pp. 8-1 to 8-21, 1988, VCH, Weinheim, Germany.

* cited by examiner

PROCESS FOR THE PRODUCTION OF MICRO AND/OR NANO PARTICLES

This application is a 371 national phase filing of PCT/IB01/01780 filed Sep. 27, 2001, and claims priority to a Swiss application No. 1209/01 filed Jul. 2, 2001.

FIELD OF THE INVENTION

This invention is particularly suitable to process solids that are soluble in liquid solvents with boiling temperatures lower than about 120° C. and non thermolabile at process temperatures up to about 80° C., to produce said solids in form of micro and nanoparticles having dimensions ranging between 0.02 and 10 micron. A non exhaustive list of the several fields of industrial application of solids in form of micronic powders is: catalysts, metal oxides, coatings and films, cosmetics, electromagnetic components, electronic devices, pigments, ceramic composites, toners, polishing products, flame retardant materials, biopolymers, polymeric composites and pharmaceuticals.

State of the Art in the Field of the Described Invention

During the last fifteen years various techniques and apparatuses have been proposed to produce powders, based on the use of gases compressed and/or in supercritical conditions. In many cases carbon dioxide has been proposed as the process fluid. The various techniques described in the technical and patent literature can be organized in three main areas and schematized as follows:

Rapid Expansion of Supercritical Solutions (RESS). This process is based on the solubilization of the solid to be micronized in a supercritical solvent and the subsequent depressurization down to near atmospheric pressure of the formed solution and the precipitation of solute. Many variations of this process and related apparatuses have been proposed: DE 2943267, U.S. Pat. Nos. 4,582,831, 4,734,451, 4,970,093.

Its major limitation consists of the limited solubility of many solids in the supercritical solvent. The control of morphology and of particle size is also very complex.

Precipitation from a liquid solution induced by a supercritical antisolvent (several acronyms have been used ASES, SEDS, GAS and SAS) we will refer to this technique as SAS (Supercritical AntiSolvent precipitation) in the following. This technique has been detailedly described in "Supercritical antisolvent precipitation of micro and nano particles, Reverchon, 1999, J. Supercrit. Fluids, 15, 1-21. The preconditions for the application of this process are that the liquid solvent is completely soluble in the supercritical antisolvent, whereas the solid is completely insoluble in it. However, the SAS processability of many solid is problematic. But, in the cases in which micronization has been successfully performed, a fair control of morphology and of particle sizes has been obtained (ranging from sub-micronic to hundreds of micron particles). Also in this case the patent literature contains many processes and application variations. For example, it is interesting the variation proposed by Hanna and York that used some different arrangements of coaxial injectors for the simultaneous mixing and atomization of the supercritical antisolvent and the liquid solution (operating in this manner it is possible to obtain a mechanical contribution to the formation of particles due to the velocity of the two flows at the exit of the injector). The patents presented in the literature differ for the application or for the fluids used (for examples, is proposed the use of an organic solvent and a supercritical antisolvent, or of solvent and antisolvent both in the supercritical conditions, or a liquid solution a second solvent and a supercritical antisolvent—U.S. Pat. No. 6,063,138) or small variations of the apparatus are proposed to optimize its use in the micronization of different substances.

Particles Generation from Gas Saturated Solutions (PGSS). In this field explicitly falls the patent filed by Weidner and Knez (EP 744992, WO 9521688) that proposed the use of supercritical carbon dioxide to be solubilized in melt polymers in a heated vessel. Supercritical carbon dioxide solubilizes in large quantities in many polymers inducing also their liquefaction (due to the lowering of the glass transition temperature). The polymeric solution obtained in this manner is sent to an injector and sprayed in a vessel operated at a lower pressure with the formation of polymer droplets that return in the solid state due to cooling induced by carbon dioxide. The minimun documented diameter of the particles produced by this technique is 7.8 micron.

Processes that have many similarities with PGSS are many spray coating processes proposed in the patent literature (U.S. Pat. Nos. 5,057,342, 5,066,522, 5,009,367, 5,106,650, 5,211,342, 5,374,305, 5,466,490), even if the scope of this processes is different from the scope of the present invention and is to produce very small droplets of coloring matter to improve the performance of coatings. The supercritical fluid in this case is use to reduce the viscosity of the solution to be sprayed. Another characteristic that is claimed in these patents is the reduction or the elimination of volatile organic compounds (VOC). In some of these patents the same process is proposed to produce powders by spraying.

Another process that is for some respects connected to PGSS is the one proposed by Sievers and coworkers (EP 677332, U.S. Pat. Nos. 5,639,441, 6,095,134). These authors propose a process in which a acqueous solution and a flow of carbon dioxide are put in contanct in a low volume tee element (with an internal volume lower than 1 microliter). The immiscible mixture of the liquid and of the supercritical fluid (defined by the authors a suspension, an emulsion, a micellar system or a dispersion) is sent to a capillary nozzle (a long thin tube with an internal diameter of, for example, 125 micron), very small droplets are formed that evaporate and produce a powder. The examples proposed in the patents and the scientific papers published by the authors are restricted to the use water as the liquid solvent.

The new process that is proposed in the present invention is referred, instead, to the formation of solutions formed by carbon dioxide and liquid solvents in which the solute is solubilized and to their subsequent atomization. The formation of the liquid solution containing carbon dioxide is regulated by the thermodynamics of pressurized fluids and by the connected vapor liquid equilibria, and is not related to heating and melting of solids. Practically, all liquid solvents can be used and particles smaller than the ones obtainable with the previous patented processes can be produced.

DESCRIPTION OF THE INVENTION

The invention consists of a new and more efficient process and of an apparatus to perform atomization assisted by carbon dioxide to produce nanometric and micrometric particles. Using this process and the proposed apparatus it is possible to control the mean particle size and particle size distribution of particles; with the unexpected possibility of obtaining mean diameters between about 0.02 (20 nanometers) and 10 micron never obtained before using processes based on the use of supercritical fluids. Due to the large range of operating conditions and the possibility of producing particles with a mean diameter included in a large range of dimensions, using this invention it will be possible:

- to substitute many of the existing micronization processes based on the use of organic solvents;
- to operate using the same apparatus either using organic solvents either using water, thus, enlarging the range of applicability of techniques previously described in the literature.

Carbon dioxide is solubilized in a liquid solution (formed by one or more solvents containing a solid solute) in a packed bed (saturator) formed by a vessel capable of operating under pressure. Carbon dioxide could be compressed, liquid or supercritical. A preferred requisite is that at process conditions the liquid solvent or solvents mixture show a low solubility in carbon dioxide.

The saturator is charged with metallic or ceramic packings (for example, Rashig rings or perforated saddles) with the aim of obtaining a very large contacting surface between the liquid and the gas and, thus, favors the dissolution of gas in the liquid. The scope is to dissolve carbon dioxide in the liquid up to concentrations near to those of solubility equilibrium, at the operating conditions of pressure and temperature.

The quantity of carbon dioxide that can dissolve in the liquid, at the operating conditions, can be comprised between 0.01 and about 0.50, preferably between 0.02 and 0.2, in terms of molar fractions. However, carbon dioxide can be added in quantities slightly larger than the foreseen equilibrium values due to the uncertainty in these values and to assure that the maximum quantity of carbon dioxide is dissolved in the liquid (thus, maximizing the process performance).

A solution is obtained, formed by a liquid phase that contains the solid solute and carbon dioxide.

This solution is atomized through a thin wall injector having one or more holes and depressurized down to near atmospheric conditions. Operating in this manner, micronic and/or submicronic droplets are formed, that rapidly evaporate in the precipitator put downstairs the injector. This operation is favoured by the heating of precipitator and by the use of a stream of heated inert gas (nitrogen, argon, air) added in the precipitation chamber.

Solid particles produced by evaporation of the liquid droplets are forced to move through the precipitator and collected at the bottom; whereas, inert gas, liquid vapors and carbon dioxide are sent to a separator to recover the liquid and to discharge gases. A system to recover and recycle carbon dioxide to be performed by cooling and recompression of $CO_2$ can be added (closed loop operation).

Key parts of the apparatus for successful processing and the production of particles as claimed in the present invention are these parts in all the possible process combinations:
a) saturator containing packings that assure the contact and the equilibrium between the phases;
b) a thin wall injector with hole diameters between 10 and 500 micron, preferably between 20 and 200 micron.
c) a flux conveyor, put inside the precipitator that impresses a spiraling direction to gas +powder in the precipitator and favors the deposition of powder at the bottom of the precipitation chamber.

Powders obtained using the described method can be amorphous or crystalline depending on the solute characteristics, on the used solvent and on the process conditions during precipitation.

FIGURES DESCRIPTION

Figure 3:
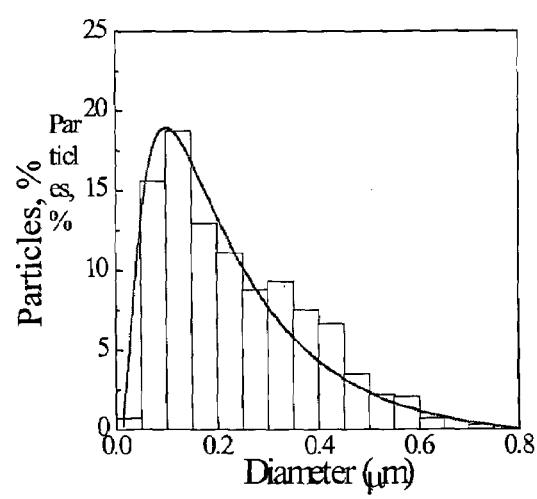
Figure 4:
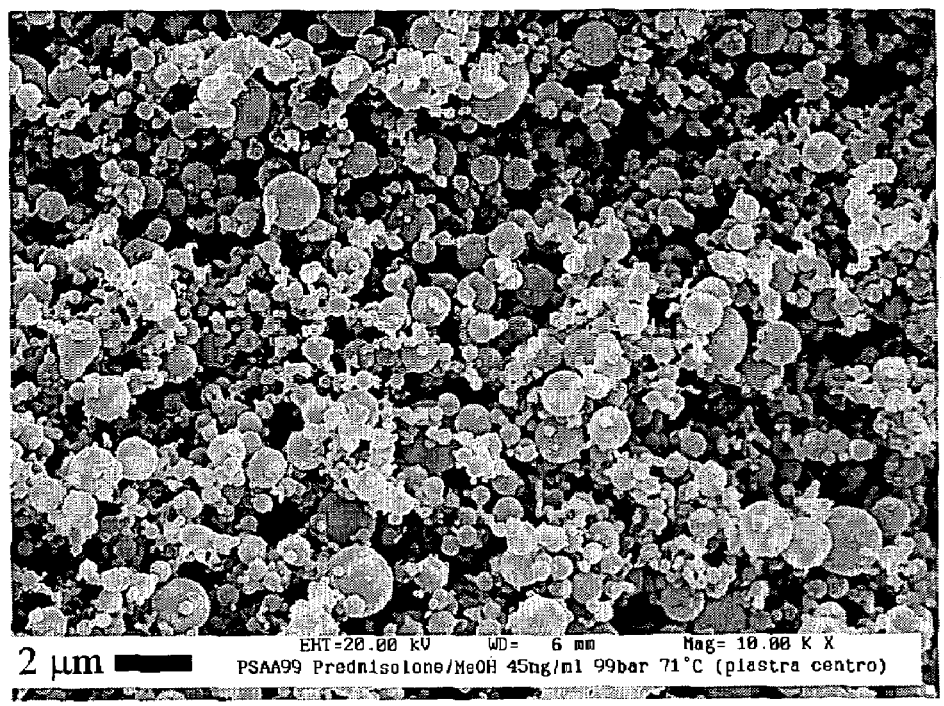

FIG. 1: Schematic representation of the apparatus
FIG. 2: Scanning Electron Microscope (SEM) image of micronized Yttrium Acetate.
FIG. 3: Particle size distribution curve related to FIG. 2.
FIG. 4: SEM image of micronized Prednisolone.

In FIG. 1 three parallel lines are drawn and indicated with numbers 1, 2 and 3 and related to the delivery of inert gas, carbon dioxide and liquid solution, respectively.

On line 1:
St1: inert gas storage vessel; M1: manometer; S1: heat exchanges, with thermal regulation system, T1;

On line 2:
St2: carbon dioxide storage vessel; S2: first thermostated bath for carbon dioxide (cooler); P2: pump; S2-1: second thermostated bath for carbon dioxide (heater).

On line 3:
St3: liquid solution storage vessel; P3: pump; S3: thermostated bath (heater).

Other parts of the apparatus are: Sat: saturator, and the related thermal regulation system T; Ip: thin wall injector; Pr: precipitator (powder collection chamber), and the related thermal regulation system T; internal pressure regulation system (M: manometer+check valve), Cf: flux conveyor; Sr: cooled separator; C: dry test meter.

Figure 2:
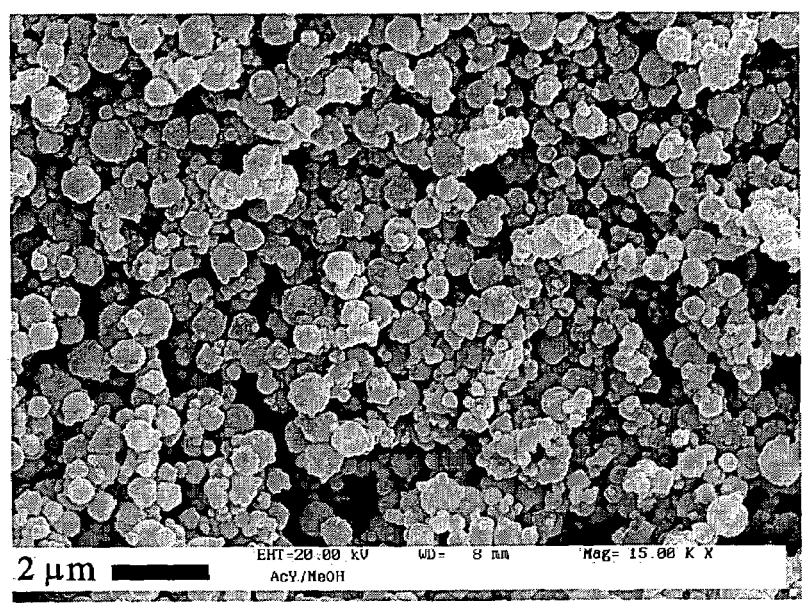

SEM image in FIG. 2 has been taken at an enlargement of 15000×.

From SEM image (in FIG. 2) is possible to obtain the particle size distribution (FIG. 3) using an image analysis software. This distribution is reported as an histogram: % of particles vs particles diameter. Minimum diameter 0.02 micron; maximum diameter: 0.72 micron.

SEM image in FIG. 4 has been taken at an enlargement of 10000×.

DETAILED DESCRIPTION OF THE APPARATUS AND OF THE PROCESS SCHEME

The apparatus used in the present invention contains two pressure lines used to deliver: the liquid solution Lq and the gas compressed, liquid or supercritical Lg. The third line works at pressures near to atmospheric and delivers a heated gas used to favor liquid evaporation in the precipitator.

Liquid line Lq is formed by a storage vessel St3 that contains the solution (liquid+solute) connected to a high pressure dosing pump P3 that can deliver a constant flow of liquid up to an operating pressure of 350 bar. The liquid is sent to a heat exchanger S3 where it is pre-heated to temperatures between 50 and 90° C. and then to the saturator Sat.

The flux of carbon dioxide compressed, liquid or supercritical, is obtained by delivering carbon dioxide from a storage tank to a high pressure dosing pump that has been modified to allow the use of compressible fluids and that can deliver constant flows of carbon dioxide up to an operating pressure of 350 bar. Carbon dioxide passes through a heat exchanger S2-1 to be heated at temperatures between 40 and 90° C., then, is sent to the saturator Sat.

The two flows (liquid solution and carbon dioxide) are mixed in the saturator Sat, that is formed by a thermostated tank that can operate up to 350 bar and is charged with adequate packing elements, for example, Rashig rings, perforated saddles or organized packings, whose scope is to assure a prolonged contact between the two phases (liquid and dense gas).

The saturator guarantees a large surface and a contacting time sufficient to allow the solubilization of carbon dioxide in the liquid up to near equilibrium conditions at the temperature and pressure of operation. However, a slight excess of carbon dioxide can be used with respect to the foreseen equilibrium value to assure the obtainment of saturation conditions.

The solution formed in the saturator is sent to the thin wall injector that connects the saturator and the precipitator (powder collection chamber) that operates at pressures near to atmospheric of under reduced pressure.

The thin wall injector Ip is formed by one or more holes having diameters ranging from 20 to 200 micron realized on a thin stainless steel wall. This kind of injector concentrates all the pressure drop (difference in pressure) between the saturator and the precipitator in the injection point to obtain an efficient spray. The spray will be formed by very small droplets. The mean diameter of the formed droplets will be particularly small since, we think that carbon dioxide during atomization blows off the liquid phase in which it was dissolved (decompressive atomization). The precipitation chamber Pr is a cylindrical thermostated vessel in which besides carbon dioxide and the liquid solution, the warm inert gas (nitrogen, argon, air) is delivered co-currently after pre-heating in a heat exchanger S1 up to 100° C.; the scope is to shorten the droplets evaporation process.

Solid particles that are formed as a consequence of liquid evaporation travel together with gas in the precipitator and form a bi-phasic flow (for example: powder, carbon dioxide, nitrogen and vapors of the liquid solvent) the is directed to the bottom of the precipitator by the helicoidal flux conveyor Cf inserted in the chamber.

The flux conveyor Cf is formed, for example, by a metallic propeller that impresses an ordered motion to the mixture gases +solid. It allows the exit of the gases from the bottom of the precipitator and the collection of the powder on a sintered stainless steel frit, put on the bottom of the precipitator. Alternatively, it is possible the electrostatic collection of powders.

Gases at the exit of the precipitator are sent to a cooled separator Sr put downstream the precipitator, in which the liquid solvent is condensed and recovered whereas; the remaining gas mixture is discharged at the exit of the apparatus.

Flow meters, temperature and pressure indicators and temperature controllers complete the apparatus.

EXAMPLES

Example 1

Production of nanoparticles of Yttrium Acetate (a superconductor precursor-AcY) by precipitation from a solution with Methyl alcohol having a concentration ranging between 2 and 50 mg AcY/ml Methanol (preferably, ranging between 15 and 25 mg AcY/mg Methyl alcohol) using the carbon dioxide assisted atomization process described in the present invention; at pressures between 80 and 140 bar (preferably, between 85 and 100 bar) and at temperatures ranging between 60 and 95° C. (preferably, between 65 and 80° C.). We used a thin wall injector with a diameter ranging between 60 and 100 micron (preferably, 80 micron) having a single hole. The liquid solution flow rate can range from 1 to 7 g/min (preferably, 3 g/min); carbon dioxide flow rate can range between 3 and 12 g/min (preferably, 6.5 g/min). An example of the produced nanoparticles is reported in FIG. 2, where a SEM image of AcY particles is proposed.

The obtained particles are spherical, amorphous and their mean diameter and particle size distribution are reported in FIG. 3.

Example 2

Production of micronic particles of Diphenylhydantoin by precipitation from a Methyl alcohol solution for concentrations ranging between 2 and 15 mg Diphenylhydantoin/ml Methyl alcohol, using the carbon dioxide assisted atomization process described in the present invention; at pressures between 75 and 120 bar (preferably between 90 and 100 bar) and at temperatures between 60 and 95° C. (preferably, between 65 and 75° C.). We used a thin wall injector with a diameter ranging between 60 and 100 micron (preferably, 80 micron) having a single hole. The liquid solution flow rate can range from 2 to 10 g/min (preferably, 4 g/min); carbon dioxide flow rate can range between 3 and 10 g/min (preferably, 7 g/min). The resulting particles are spherical and their mean diameter ranges between 0.8 and 2.5 micron.

Example 3

Production of micro-crystals of Nifedipine by precipitation from a solution with Acetone for concentrations ranging between 2 and 150 mg Nifedipine/ml Acetone, using the carbon dioxide assisted atomization process described in the present invention; at pressures between 60 and 80 bar (preferably between 60 and 70 bar) and at temperatures between 70 and 100° C. (preferably, between 70 and 80° C.). We used a thin wall injector with a diameter ranging between 60 and 100 micron (preferably, 80 micron) having a single hole. The liquid solution flow rate can range from 2 to 9 g/min (preferably, 5 g/min); carbon dioxide flow rate can range between 4 and 14 g/min (preferably, 9 g/min). Their mean diameter ranges between 1 and 5 micron.

Example 4

Production of Rifampicin microparticles by precipitation from a solution with Alcohol for concentrations ranging between 2 and 30 mg Rifampicin/ml Alcohol, using the carbon dioxide assisted atomization process described in the present invention; at pressures between 80 and 130 bar (preferably between 90 and 105 bar) and at temperatures between 50 and 80° C. (preferably, between 50 and 60° C.). We used a thin wall injector with a diameter ranging between 60 and 100 micron (preferably, 80 micron) having a single hole. The liquid solution flow rate can range from 2 to 9 g/min (preferably, 5 g/min); carbon dioxide flow rate can range between 4 and 14 g/min (preferably, 8 g/min). The resulting particles are spherical amorphous and their mean diameter ranges between 0.5 and 2.0 micron.

Example 5

Production of Prednisolone microparticles by precipitation from a solution with Methyl alcohol for concentrations ranging between 1 and 65 mg Prednisolone/ml Methyl Alcohol, (preferably, between 3 and 50 mg/ml Methyl alcohol) using the carbon dioxide assisted atomization process described in the present invention; at pressures between 80 and 120 and at temperatures between 60 and 85° C. We used a thin wall injector with a diameter ranging between 60 and 100 micron (preferably, 80 micron) having a single hole. The liquid solution flow rate can range from 5 to 15 g/min (preferably, 8 g/min); carbon dioxide flow rate can range between 2 and 8 g/min (preferably, 3 g/min). An example of microparticles obtained using the described process is reported in FIG. 4, where a SEM image of prednisolone particles is showed. These particles have been obtained operating at 98 bar, 71° C. and 45 mg/ml Methyl alcohol; they are spherical, amorphous and their mean diameter is 1.1 micron.

The invention claimed is:

1. A process for producing micro and/or nano particles of solids with a mean diameter ranging between 0.01 and 100 micrometers, the process comprising the steps of:
    solubilizing a solid in a liquid solvent or a mixture of liquid solvents, the liquid solvent or the mixture of liquid solvents having very low or zero solubility in carbon dioxide under conditions with temperature between 30 and 100° C. and pressure between 50 and 240 bar;
    solubilizing a dense carbon dioxide in the liquid solvent or the mixture of liquid solvents, the dense carbon dioxide being compressed, liquid or supercritical, wherein solubilization takes place in a saturation chamber loaded with high surface packings at process conditions with temperature between 30 and 100° C. and pressure between 50 and 240 bar;
    injecting a thus obtained solution through a thin wall injector into a precipitation vessel operated at pressures near atmospheric pressure; and
    recovering produced powders.

2. The process according to claim 1, wherein process conditions comprise temperature between 40 and 90° C. and pressure between 60 and 150 bar to yield particles having a mean diameter ranging between 0.02 and 10 micrometers.

3. The process according to claim 1, wherein a solid solute formed by more than one compound is used to obtain an extremely uniform co-precipitate.

4. The process according to claim 1, wherein the liquid solvent is chosen from the group consisting of Methyl alcohol, Ethyl alcohol, Propyl alcohol, Acetone, Dichloromethane, Chloroform, water and combinations thereof in any proportion.

5. The process according to claim 1, wherein the solid is from a category of solid compounds comprising active principles for pharmacological use, active principles for veterinary use, superconductor precursors, catalysts precursors or combinations thereof.

6. The process according to claim 1, wherein the solid is chosen from the group consisting of powders that are usable in injectable suspensions, aerosolizable powders, transdermal formulations controlled release formulations and combinations thereof.

7. The process according to claim 1, wherein the solid is chosen from the group consisting of ceramics, phosphors, toners, cosmetics, conductive pastes, explosives, propellants, flame retardants, polymeric composites, pigments, polymers and metal oxides.

8. The process according to claim 1, comprising the steps of:
    solubilizing a dense carbon dioxide in a liquid solution containing a solute or solutes to be micronized, wherein solubilization is obtained in a saturator loaded with high surface packings, and further wherein the liquid solution and the dense carbon dioxide are in contact at an operation pressure and temperature for a time sufficient to favor solubilization;
    injecting a final ternary solution comprising said liquid, said solute or salutes and said dense carbon dioxide through a thin wall injector, where the final ternary solution is micronized in droplet form; and
    delivering a flow of warm inert gas to allow solid nano and/or micro particles to be formed by a droplet evaporation process.

9. The process according to claim 8, employing a liquid-solution flow range from 2 to 15 g/min.

10. The process according to claim 8, employing a carbon-dioxide flow rate range between 2 and 14 g/min.

11. The process according to claim 8, wherein the dense carbon dioxide is continuously solubilized in a liquid solution comprising the solute or solutes to be micronized.

12. An apparatus for producing micro and/or nano particles of solids with a mean diameter ran between 0.01 and 100 micrometers, comprising:
    a saturator charged with packing elements;
    a precipitator;
    a thin wall injector for forming droplets that connects the saturator and the precipitator;
    a first pressure line for delivering a liquid solution to a first heat exchanger for pre-heating the liquid solution to temperatures between 50 and 90° C., and for subsequently delivering to the saturator;
    a second pressure line for delivering a dense carbon dioxide to a second heat exchanger for heating the dense carbon dioxide to temperatures between 40 and 90° C., and for subsequently delivering to the saturator; and
    a third pressure line working at pressures near atmospheric values for delivering an inert gas to a third heat exchanger for pre-heating the inert gas up to 100° C., and for subsequently delivering to the precipitator.

13. The apparatus according to claim 12, wherein the thin wall injector has holes with diameters between 10 and 500 micrometers.

14. The apparatus according to claim 12, wherein said packings are metallic or ceramic packings.

15. The apparatus according to claim 14, wherein said packings are Raschig rings or perforated saddles.

16. The apparatus according to claim 12, further comprising a flux conveyor for favoring collections of produced powders.

17. The process according to claim 6, wherein the solid comprises antibiotics, enzymes, asthma controlling drugs, corticosteroids, chemiotherapics, anti-inflammatories or combinations thereof.

* * * * *

UNITED STATES PATENT AND TRADEMARK OFFICE
CERTIFICATE OF CORRECTION

PATENT NO.         : 7,276,190 B2
APPLICATION NO. : 10/482640
DATED              : October 2, 2007
INVENTOR(S)        : Ernesto Reverchon Page 1 of 1

It is certified that error appears in the above-identified patent and that said Letters Patent is hereby corrected as shown below:

Column 8, claim 8, line 9, "salutes" should read --solutes--; and

Column 8, claim 12, line 23, "ran between" should read --ranging between--.

Signed and Sealed this

Third Day of June, 2008

JON W. DUDAS
*Director of the United States Patent and Trademark Office*